US00PP28707P3

(12) United States Plant Patent
Giesen

(10) Patent No.: US PP28,707 P3
(45) Date of Patent: Nov. 28, 2017

(54) ***DAHLIA* PLANT NAMED 'DAHZ0012'**

(50) Latin Name: ***Dahlia* hybrid Cav.**
Varietal Denomination: DAHZ0012

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 102 days.

(21) Appl. No.: 14/757,248

(22) Filed: Dec. 10, 2015

(65) Prior Publication Data

US 2016/0205855 P1 Jul. 14, 2016

Related U.S. Application Data

(60) Provisional application No. 62/102,271, filed on Jan. 12, 2015.

(51) Int. Cl.
*A01H 5/02* (2006.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen Redden
(74) *Attorney, Agent, or Firm* — Dale Skalla

(57) ABSTRACT

A new *Dahlia* plant named 'DAHZ0012', particularly distinguished by large white full double flowers, an upright plant habit with excellent branching, dark green foliage, and good floriferousness.

1 Drawing Sheet

Latin name of the genus and species of the plant claimed: *Dahlia* hybrid Cav.

Varietal denomination: 'DAHZ0012'.

BACKGROUND OF THE NEW PLANT

The present invention comprises a new *Dahlia*, botanically known as *Dahlia* hybrid and hereinafter referred to by the variety name 'DAHZ0012'.

'DAHZ0012' is a product of a planned breeding program. The new cultivar has large white full double flowers, an upright plant habit with excellent branching, dark green foliage, and good floriferousness.

'DAHZ0012' originates from a sibling cross hybridization in a controlled breeding program in Andijk, Netherlands. The pollinations were made in May 2008.

The female parent was an unpatented, proprietary hybrid seedling identified as 'D08-170-1', having white flower color, medium green foliage and a smaller plant size than 'DAHZ0012'.

The male parent of 'DAHZ0012' was an unpatented, proprietary plant identified as 'D06-261', with white flowers, large flower size, dark green leaves, and a not good branching plant habit.

The resulting the seed sown in May 2009 and 'DAHZ0012' was selected as one flowering plant within the progeny of the stated cross in September 2009 in a greenhouse in Andijk, Netherlands.

The first act of asexual reproduction of 'DAHZ0012' was accomplished when vegetative cuttings were propagated from the initial selection in April 2010 in a controlled environment in Andijk, Netherlands.

BRIEF SUMMARY OF INVENTION

Horticultural examination of plants grown from cuttings of the plant initiated in April 2011 in Andijk, Netherlands, and continuing thereafter, has demonstrated that the combination of characteristics as herein disclosed for 'DAHZ0012' are firmly fixed and are retained through successive generations of asexual reproduction.

'DAHZ0012' has not been observed under all possible environmental conditions. The phenotype may vary significantly with variations in environment such as temperature, light intensity and day length.

A Plant Breeder's Right for this cultivar was applied for in the European Community Plant Variety Office (CPVO) on May 5, 2014, No. 2014/1208. 'DAHZ0012' has not been made publicly available more than one year prior to the filing of this application.

The following traits have been repeatedly observed and are determined to be basic characteristics of the new variety. The combination of these characteristics distinguishes this *Dahlia* as a new and distinct variety.

BRIEF DESCRIPTION OF THE PHOTOGRAPHS

Figure 1:
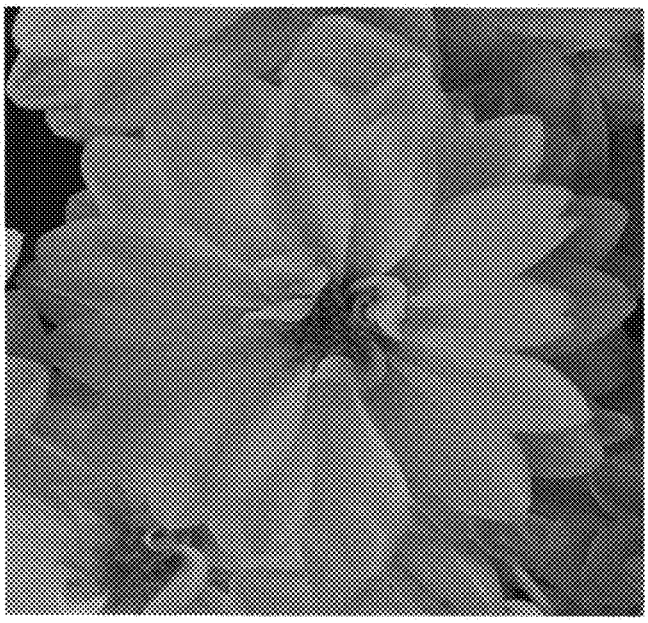
Figure 2:
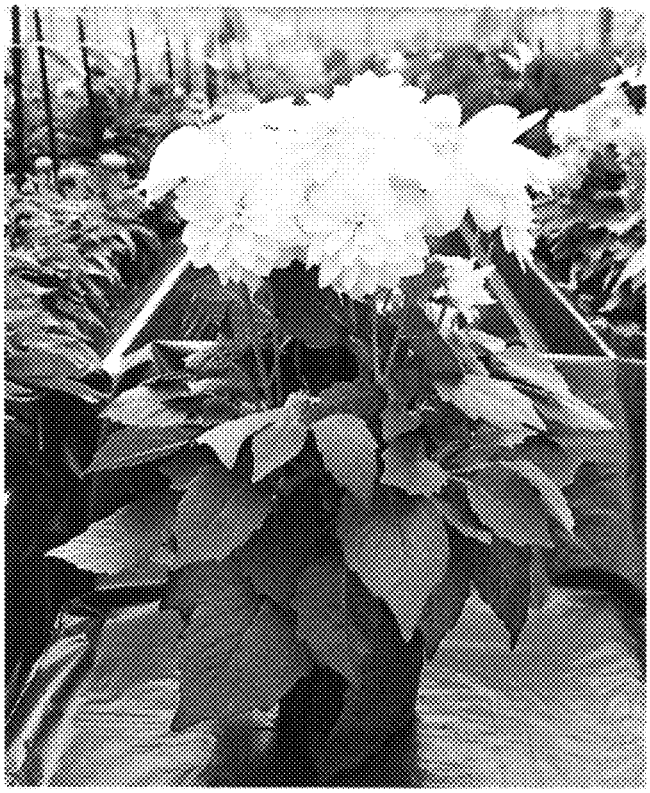

The accompanying photographic drawings show typical flower and foliage characteristics of 'DAHZ0012' with colors being as true as possible with an illustration of this type. The photographic drawings show in FIG. 1, a close-up of the flowers and in FIG. 2, a flowering potted plant of the new variety.

DETAILED BOTANICAL DESCRIPTION

The aforementioned photographs were taken at May 2013 in Andijk, Netherlands. The plants were growing in 13 cm pots on benches in a greenhouse. They were about 14 weeks of age.

The plant descriptions and measurements were taken in Enkhuizen, The Netherlands, on Sep. 4, 2014, from 14-week-old plants that were growing outdoors in the trial field.

Color references are made to The Royal Horticultural Society Colour Chart (R.H.S.) 2001.

TABLE 1

DIFFERENCES BETWEEN THE NEW VARIETY 'DAHZ0012' AND A SIMILAR VARIETY

| | 'DAHZ0012' | 'Dahlia XXL Yucatan (White)', not patented |
|---|---|---|
| Overall flower color: | Paper white | Cream white |
| Flower type or position: | Large flowers with medium long stem | Extra large flowers with short stem |
| Foliage: | Dark green leaf | Medium dark green leaf |
| Plant size or habit: | Upright compact plant habit | Semi upright with very compact plant habit |

Plant:

*Form, growth and habit*.—Round, tight and compact; freely branching.

*Plant height*.—28 cm.

*Plant height (inflorescence included)*.—34 cm.

*Plant width*.—42 cm.

*Garden performance and tolerance to weather*.—Good.

*Crop time to flowering*.—About 9-12 weeks.

Roots:

*Number of days to initiate and develop roots*.—About 21-28 days at about 21 degrees C.

*Type*.—Fine, fibrous, free branching.

*Color*.—RHS N155A.

Foliage:

*Arrangement*.—Opposite, simple and sometimes pinnate.

*Immature, leaf color, upper surface*.—Between RHS 137A and 137B.

*Lower surface*.—RHS 137B.

*Mature, leaf color, upper surface*.—RHS 147A.

*Lower surface*.—RHS 147B but slightly more greyish.

*Type*.—Mostly simple, some are pinnate.

*Length*.—8-10.5 cm, including petiole.

*Width*.—4-7.5 cm.

*Shape*.—Ovate.

*Base shape*.—Attenuate.

*Apex shape*.—Acute.

*Margin*.—Dentate.

*Texture, upper surface*.—Glabrous, rough texture.

*Lower surface*.—Glabrous.

*Venation color, upper*.—RHS 147A.

*Lower*.—RHS 147C.

*Petiole color*.—RHS 144B and RHS 137A on the edges.

*Petiole length*.—Up to 2.2 cm.

*Diameter of petiole*.—0.3 cm at the mid-section.

*Texture*.—Glabrous.

Stem:

*Average quantity of main branches per plant*.—About 8, each with 3 secondary branches.

*Color of stem*.—RHS 145A.

*Length of stem*.—20-23 cm.

*Diameter*.—0.5 cm at the mid-section.

*Length of internodes*.—5-6 cm.

*Texture*.—Glabrous.

*Color of peduncle*.—RHS N143A.

*Length of peduncle*.—6-7 cm.

*Peduncle diameter*.—0.4 cm.

*Texture*.—Glabrous.

Inflorescence:

*Type*.—Inflorescences borne on terminals above foliage; double.

*Blooming habit*.—Continuous throughout the growing season.

*Average quantity of inflorescences per plant*.—70, with buds.

*Average quantity of inflorescences per lateral stem*.—5.

*Lastingness of individual blooms on the plant*.—7-12 days.

*Fragrance*.—None.

Bud (just before opening):

*Color*.—From the base to the top: RHS 144A.

*Length*.—1.2 cm, at the base of the phyllaries (excluded).

*Width*.—1.5 cm.

*Shape*.—Completely round to bell-shaped with unfolding of the rays.

Immature inflorescence:

*Diameter*.—About 4.5-6 cm.

*Color of ray florets, upper surface*.—RHS 20A.

*Lower surface*.—Base is RHS 157D.

Mature inflorescence:

*Diameter*.—8.0-10 cm.

*Depth*.—4 cm.

*Total diameter of 'disc'*.—0.5 cm.

*Recepticle height*.—0.2 cm.

*Recepticle diameter*.—1.3-1.4 cm.

Ray florets:

*Average quantity of florets*.—About 100.

*Color of florets, upper surface*.—RHS 157A.

*Lower surface*.—RHS 157C.

*Length*.—3.0-3.4 cm.

*Width*.—1-2.2 cm.

*Shape*.—Broadly oval.

*Base shape*.—Rolled to fused just at the base, acute.

*Apex shape*.—Mucronulate.

*Margin*.—Entire.

*Texture, upper surface*.—Papillose; glabrous.

*Lower surface*.—Papillose; glabrous.

*Number of petaloids*.—1-5 per ray floret.

*Color of petaloids, upper surface*.—RHS 155D.

*Lower surface*.—RHS 157A.

*Length*.—1.1-1.5 cm.

*Width*.—0.4 -0.7 cm.

*Shape*.—Lanceolate, sometimes twisted.

*Apex shape*.—Obtuse.

Disc florets:

*Average quantity of florets*.—About 0 to 5 quantities.

*Color of florets*.—RHS 157A.

*Length*.—0.6-0.8 cm.

*Width*.—0.3 cm.

*Shape*.—Tube-shaped.

*Apex shape*.—Acute, 5-pointed.

Phyllaries:

*Types of phyllaries*.—2 different types; phyllaries are arranged in 2-3 whorls.

*Phyllaries of the lower whorl are green and thicker*.—

*Average quantity*.—About 5.

*Color, upper surface*.—RHS 136A.

*Lower surface*.—RHS 135B.

*Length*.—1.2 cm.

*Width*.—0.8 cm.

*Shape*.—Ovate.

*Base shape*.—Shortly attenuate.

*Apex shape*.—Acute.
*Margins*.—Entire.
*Texture, upper surface*.—Glabrous.
*Lower surface*.—Glabrous.
*Phyllaries in the upper whorl are mostly transparent*.—
*Average quantity*.—22-27.
*Color, upper surface*.—RHS 143B.
*Lower surface*.—RHS 143B.
*Length*.—1.7 cm.
*Width*.—0.9 cm.
*Shape*.—Ligulate.
*Base shape*.—Fused.
*Apex shape*.—Acute.
*Margins*.—Entire.
*Texture, upper surface*.—Glabrous.
*Lower surface*.—Glabrous.

Reproductive organs: Not always present as there are not always disc florets.

*Gyneocium*.—Present on ray and disc florets.
*Pistil quantity*.—1 per floret.
*Length*.—1.2 cm.
*Style color*.—RHS 145B.
*Style length*.—0.9 cm.
*Stigma color*.—RHS 21C.
*Stigma shape*.—Bi-furchate (bi-lobed).
*Ovary color*.—RHS 145B.
*Andreocium*.—Present on disc florets only.
*Stamens quantity*.—5 united.
*Color of filaments*.—RHS 150A.
*Length filaments*.—0.2 cm.
*Anther color*.—RHS 21A.
*Anther length*.—0.3 cm.
*Color of pollen*.—RHS 21A. There were no seeds observed. There were no specific pest and disease resistance observed.

What is claimed is:

1. A new and distinct variety of *Dahlia* plant named 'DAHZ0012', substantially as illustrated and described herein.

* * * * *